US011629360B2

(12) United States Patent
Dominici et al.

(10) Patent No.: US 11,629,360 B2
(45) Date of Patent: Apr. 18, 2023

(54) METHOD FOR PRODUCTION OF MODIFIED CELLS EXPRESSING HOX AND MODIFIED CELLS OBTAINED BY THE METHOD

(71) Applicants: Massimo Dominici, Ferrara (IT); Olivia Candini, Crevalcore (IT)

(72) Inventors: Massimo Dominici, Ferrara (IT); Olivia Candini, Crevalcore (IT)

( * ) Notice: Subject to any disclaimer, the term of this patent is extended or adjusted under 35 U.S.C. 154(b) by 0 days.

(21) Appl. No.: 15/329,249

(22) PCT Filed: Jul. 30, 2015

(86) PCT No.: PCT/IB2015/055752
§ 371 (c)(1),
(2) Date: Jan. 26, 2017

(87) PCT Pub. No.: WO2016/016829
PCT Pub. Date: Feb. 4, 2016

(65) Prior Publication Data
US 2017/0218396 A1    Aug. 3, 2017

(30) Foreign Application Priority Data

Jul. 30, 2014    (IT) .......................... MO2014A000227

(51) Int. Cl.
*C12N 15/86* (2006.01)
*C07K 14/47* (2006.01)

(52) U.S. Cl.
CPC .......... *C12N 15/86* (2013.01); *C07K 14/4702* (2013.01); *C12N 2740/13043* (2013.01)

(58) Field of Classification Search
CPC ...................... C12N 15/86; C12N 2740/13043
See application file for complete search history.

(56) References Cited

PUBLICATIONS

Lawrence et al. (1999) Frequent co-expression of the HOXA9 and MEIS1 homeobox genes in human myeloid leukemias. Leukemia, 13:1993-1999 (Year: 1999).*
Care et al. (1999) Enforced expression of HOXB7 promotes hematopoietic stem cell proliferation and myeloid-restricted progenitor differentiation. Oncogene, 18:1993-2001 (Year: 1999).*
Care et al. (2001) HOXB7: A Key Factor for Tumor-associated Angiogenic Switch. Cancer Research, 61:6532-6539 (Year: 2001).*
Candini et al. (2015) Mesenchymal Progenitors Aging Highlights a miR-196 Switch Targeting HOXB7 as Master Regulator of Proliferation and Osteogenesis. Stem Cells, 33:939-950 (Year: 2015).*
Friedl et al. (2007) Undifferentiated human mesenchymal stem cells (hMSCs) are highly sensitive to mechanical strain: transcriptionally controlled early osteo-chondrogenic response in vitro. OsteoArthritis and Cartilage, 15:1293-1300 (Year: 2007).*
Keating, A. (2006) Mesenchymal stromal cells. Current Opinion in Hematology, 13(6):419-425 (Year: 2006).*
Gao et al. (2015) Homeobox B7 promotes the osteogenic differentiation potential of mesenchymal stem cells by activating RUNX2 and transcript of BSP. International Journal of Clinical and Experimental Medicine, 8(7):10459-10470 (Year: 2015).*
Satija et al. (2007) Mesenchymal Stem Cells: Molecular Targets for Tissue Engineering. Stem Cells and Development, 16:7-23 (Year: 2007).*
Honda et al. (2013) Guiding the osteogenic fate of mouse and human mesenchymal stem cells through feedback system control. Scientific Reports, 3(3420):1-9 (Year: 2013).*
NM_004502.3 (*Homo sapiens* homeobox B7 (HOXB7), mRNA, NCBI Reference Sequence, priority to Feb. 26, 2014, 4 pages) (Year: 2014).*
Wagner et al., Aging and Replicative Senescence Have Related Effects on Human Stem and Progenitor Cells. (2009) PLOS One 4(6): e5846, pp. 1-13 (Year: 2009).*
Care et al. Enforced expression of HOXB7 promotes hematopoietic stem cell proliferation and myeloid-restricted progenitor differentiation (1999) Oncogene, 18: 1993-2001. (Year: 1999).*
Care et al. HOXB7: A Key Factor for Tumor-associated Angiogenic Switch, (2001) Cancer Research, 61:6532-6539. (Year: 2001).*
Satija et al. Mesenchymal Stem Cells: Molecular Targets for Tissue Engineering. (2007) Stem Cells and Development, 16: 7-23 (Year: 2007).*
Yin et al., (2014). Proceedings of the International society for stem cell research, Vancouver, BC, Canada; Poster presentation Jun. 2014 (Year: 2014).*
Simonson et al., Telomerase expression extends the proliferative life-span and maintains the osteogenic potential of human bone marrow stromal cells. Nature Biotechnology (2002), 20: 592-596 (Year: 2002).*
Okamoto et al., Clonal heterogeneity in differentiation potential of immortalized human mesenchymal stem cells. Biochemical and Biophysical Research Communications (2002), 295: 354-361 (Year: 2002).*
Balducci et al., Immortalization of human adipose-derived stromal cells: production of cell lines with high growth rate, mesenchymal marker expression and capability to secrete high levels of angiogenic. Stem Cell Research and Therapy (2014), 5(63): 1-15, published May 6, 2014 (Year: 2014).*
Nishioka et al., Immortalization of bone marrow-derived human mesenchymal stem cells by removable simian virus 40T antigen gene: Analysis of the ability to support expansion of cord blood hematopoietic progenitor cells International Journal of Oncology (2003), 23: 925-932 (Year: 2003).*
Torsvik et al., (2010) Spontaneous malignant transformation of human mesenchymal stem cells reflects cross-contamination: putting the research field on track—letter. Cancer Research 70(15): 6393-6396 (Year: 2010).*
Go et al., Forced expression of Sox2 or Nanog in human bone marrow derived mesenchymal stem cells maintains their expansion and differentiation capabilities. Experimental Cell Research (2008), 314: 1147-1154 and Supplemental Material (Year: 2008).*

(Continued)

*Primary Examiner* — Samuel C Woolwine
*Assistant Examiner* — Catherine Konopka
(74) *Attorney, Agent, or Firm* — Themis Law; Franco A. Serafini; David M. Fortner

(57) ABSTRACT

A cell modified for obtaining increased proliferative capacity, decreased aging and enhanced regenerative capacity, its modification involving HOXB7 overexpression obtained using a gene vector that can insert the coding sequence into the cell, thereby affording increased protein production.

6 Claims, 12 Drawing Sheets
Specification includes a Sequence Listing.

(56) References Cited

PUBLICATIONS

Jacome et al., Lentiviral-mediated Genetic Correction of Hematopoietic and Mesenchymal Progenitor Cells From Fanconi Anemia Patients. Molecular Therapy (2009) 147(6): 1083-1092 (Year: 2009).*

Han et al., Nanog Reverses the Effects of Organismal Aging on Mesenchymal Stem Cell Proliferation and Myogenic Differentiation Potential. Stem Cells (2012), 30: 2746-2759 (Year: 2012).*

Gersch R P et al: "Reactivation of Hox gene expression during bone regeneration", Journal of Orthopaedic Research, Orthopaedic Research Society, US, vol. 23, No. 4, Jul. 1, 2005 (Jul. 1, 2005), pp. 882-890, XP027720570, ISSN: 0736-0266 p. 883, col. 1, paragraph 3; p. 884, col. 2, paragraph 1; p. 888, col. 1, paragraph 1; p. 889, col. 1.

Alessandra Caré et al: "HOXB7: A Key Factor for Tumor-associated Angiogenic Switch 1", Cancer Research, vol. 61, Sep. 1, 2001 (Sep. 1, 2001) pp. 6532-6539, XP055182025, p. 6532, col. 2, paragraphs 4,6.

Y. Yaron et al: "Identification of Novel Functional Regions Important for the Activity of HOXB7 in Mammalian Cells", The Journal of Immunology, vol. 166, No. 8, Apr. 15, 2001 (Apr. 15, 2001), pp. 5058-5067, XP055182123, ISSN: 0022-1767, DOI: 10.4049/jimmunol.166.8.5058 p. 5059, col. 1, paragraph 1; p. 5059, col. 1, paragraphs 4,5; p. 5059, col. 2, paragraph 2; p. 5061, col. 2, paragraph 5; p. 5066; figure 10.

Pablo Villavicencio-Lorini et al:"Homeobox genes dll-d13 and a13 control mouse autopod cortical bone and joint formation", Journal of Clinical Investigation, vol. 120, No. 6, Jun. 1, 2010 (Jun. 1, 2010), pp. 1994-2004, XP055182188, ISSN: 0021-9738, DOI: 10 1172/JC141554 p. 1994, col. 2, paragraph 2; p. 1995, col. 1, paragraph 2.

Cavalcanti Bitu C et al: "675 Overexpression of HOXB7 homeobox gene in oral cancer induces cellular proliferation and is associated with poor prognosis", European Journal of Cancer. Supplement, Pergamon, Oxford, GB, vol. 8, No. 5, Jun. 1, 2010 (Jun. 1, 2010), p. 170, XP027105902, ISSN: 1359-6349 the whole document.

Alessandra Care et al: "Enforced expression of HOXB7 promotes hematopoietic stem cell proliferation and myeloid-restricted progenitor differentiation", Oncogene, vol. 18, No. 11, Jan. 1, 1999 (Jan. 1, 1999), pp. 1993-2001, XP055182282, ISSN: 0950-9232, DOI: 10.1038/sj.onc.1202498 p. 1994, col. 2, paragraph 1—p. 1995, col. 1; p. 1999, col. 2, paragraph 5—p. 2000, col. 1, paragraph 1; p. 2000, col. 1, paragraph 2-4.

Yeon Jeong Kim et al: "miR-196a Regulates Proliferation and Osteogenic Differentiation in Mesenchymal Stem Cells Derived From Human Adipose Tissue", Journal of Bone and Mineral Research, vol. 24, No. 5, May 1, 2009 (May 1, 2009), pp. 816-825, XP055038945, ISSN: 0884-0431, DOI: 10.1359/jbmr.081230 p. 817, col. 1, paragraphs 1,2 p. 823, col. 2, paragraph 2—p. 824, col. 1.

Simone Braig et al: "MicroRNA miR-196a is a central regulator of HOX-B7 and BMP4 expression in malignant melanoma", CMLS Cellular and Molecular Life Sciences, Birkhauser-Verlag, BA, vol. 67, No. 20, May 18, 2010 (May 18, 2010), pp. 3535-3548, XP019837901, ISSN: 1420-9071.

* cited by examiner

*FIG. 23*

|  | P- | P+ | P- versus P+ |
|---|---|---|---|
| hsa-miR-99a | 6,711825 | 5,87567 | up |
| hsa-miR-100 | 11,11023 | 10,36359 | up |
| hsa-miR-196b | 4,599639 | 2,848668 | up |
| hsa-miR-337-5p | 2,471795 | 3,256137 | down |
| hsa-miR-376b | 1,809592 | 3,134532 | down |
| hsa-miR-431 | 2,735623 | 3,580164 | down |
| hsa-miR-543 | 3,27893 | 3,978598 | down |

FIG. 24

SEQUENCE LISTING
(SEQ ID NO 2)

```
ATGAGTTCATTGTATTATGCGAATACTTTATTTTCTAAATATCCAGCCTCAAGT
TCGGTTTTCGCTACCGGAGCCTTCCCAGAACAAACTTCTTGTGCGTTTGCTTC
CAACCCCCAGCGCCCGGGCTATGGAGCGGGTTCGGGCGCTTCCTTCGCCGCC
TCGATGCAGGGCTTGTACCCCGGCGGGGGGGCATGGCGGGCCAGAGCGCG
GCCGGCGTCTACGCGGCCGGCTATGGCTCGAGCCGAGTTCCTTCAACATGC
ACTGCGCGCCCTTTGAGCAGAACCTCTCCGGGGTGTGTCCCGGCGACTCCGC
CAAGGCGGCGGGCGCCAAGGAGCAGAGGGACTCGGACTTGGCGGCCGAGAG
TAACTTCCGGATCTACCCCTGGATGCGAAGCTCAGGAACTGACCGCAAACGA
GGCCGCCAGACCTACACCCGCTACCAGACCCTGGAGCTGGAGAAAGAATTTC
ACTACAATCGCTACCTGACGCGGCGGCGGCGCATCGAGATCGCGCACACGCT
CTGCCTCACGGAAAGACAGATCAAGATTTGGTTTCAGAACCGGCGCATGAAG
TGGAAAAAGGAGAACAAGACCGCGGGCCCGGGGACCACCGGCCAAGACAGG
GCTGAAGCAGAGGAGGAAGAGGAAGAGTGA
```

METHOD FOR PRODUCTION OF MODIFIED CELLS EXPRESSING HOX AND MODIFIED CELLS OBTAINED BY THE METHOD

REFERENCE TO SEQUENCE LISTINGS

The sequence listings contained in the ASCII text file titled Seq1_ST25, created on Mar. 28, 2021 and having a size of 2.23 kB, are incorporated herein by reference.

FIELD OF THE INVENTION

The invention relates to genetic modification of human or animal eukaryotic cells by introduction of a transcription factor of the HOX family, generally for quality enhancement.

BACKGROUND ART

Stem cells isolated from a variety of sources are widely used in preclinical and clinical regenerative medicine applications, which mainly utilize their proliferative and differentiative potential (Caplan and Bruder, 2001).

Nevertheless, the molecular mechanisms underlying these two important properties of the stem cells are still being intensively investigated, because a deeper understanding thereof might lead to optimized cell therapy, providing more long-lasting stem cell action.

The regenerative potential of stem cells was found to be temporary upon infusion thereof into patients (Dominici et al., 2009; Li and Lin, 2012), suggesting that their relatively short-lasting therapeutic capacity might be caused by intrinsic and extrinsic factors, as shown for hematopoietic stem cells (Van Zant and Liang, 2012).

One of these factors may be the age-related decline in cell function. There is extensive evidence of a reduction of the proliferative and differentiative potential with aging (Alt et al., 2012; Mareschi et al., 2006; Sethe et al., 2006; Stenderup et al., 2003; Wagner et al., 2008; Zaim et al., 2012; Zhou et al., 2008).

Stem cell aging in humans is a complex and still poorly understood process, and in contrast there is an urgent need for clinical improvement and development of cell therapies, as is frequently indicated for treating degenerative diseases typical of old age.

With the understanding of the molecular mechanisms underlying this process therapeutic approaches may be optimized, thereby leading to the identification of key factors that might affect and counteract cell aging.

A number of observational studies have attempted to identify molecular markers for stem cell aging, by miRNA and gene expression profile assessment, or by trying to relate aging to the replicative senescence of cells in vitro (Alt et al., 2012; Alves et al., 2012; Bork et al., 2010; Pandey et al., 2011; Siegel et al., 2013; Wagner et al., 2009; Zhou et al., 2008). In spite of this, the genetics that underlies the age- and senescence-related impairment of stem cell properties is still poorly understood.

Molecular factors that might have a critical role in targeting specific cell behavior, thereby contrasting the effects of senescence and providing tissue protection, include Homeobox (HOX) genes.

This family of transcription factors has a key role in determining the identity and location of cells and tissues during embryonic development, and this activity likely persists during adulthood.

The activity of HOX proteins can significantly affect the behavior of stem cells by controlling their proliferation, differentiation, migration and adhesion even in response to tissue damage (Gersch et al., 2005; Leucht et al., 2008).

The role of HOX proteins in hematopoiesis has been intensively investigated using animal models of retroviral overexpression and knock-out and knock-in transgenic approaches, which provide clear evidence of their regulatory function (Argiropoulos and Humphries, 2007).

A very important effect of these transcription factors is their ability of promoting proliferation and self-renewal of bone marrow progenitors.

While forced expression of certain HOX genes might lead to the development of myeloproliferative disorders, others, such as Hoxb4, are able to induce proliferation and expansion of stem cells without causing leukemia development and have been described as useful and safe therapeutic approaches for hematopoietic stem cell manipulation for clinical applications (Sauvageau et al., 1995).

HOX proteins also have a key role in controlling the development and differentiation of bone marrow stem cells.

Most of the knowledge of HOX-mediated effects in hematopoietic cells derives from overexpression studies, because the mutations that lead to a loss of the HOX function are not apparent at the phenotypic level, as a result of the functional redundancy of the factors of this family.

These studies have shown that the overexpression of HOX genes in hematopoietic progenitors induces increased proliferation and a shift in the differentiative fate.

For instance, ectopic expression of HOXB8 reduces granulocyte differentiation and enhances monocyte differentiation, whereas overexpression of HOXA3 promotes granulocyte differentiation and blocks monocyte differentiation.

HOXA5 or HOXB6 overexpression in hematopoietic progenitors inhibits erythropoiesis, HOXA10 overexpression blocks lymphocyte differentiation and enhances monocyte differentiation.

In spite of the incontestable evidence of the key role of HOX in the development and function of bone marrow progenitors, the role of this genes during tissue regeneration and repair is poorly known (Mahdipour and Mace, 2011).

HOX transcription factors may also regulate the behavior of other stem cells, e.g. mesenchymal progenitors (Mesenchymal Stem Cells, MSC).

Observational studies in a murine model indicate that the presence of HOXB2, HOXB5, HOXB7 and HOXC4 is associated with cell expansion and self-renewal (Phinney et al., 2005), whereas other HOX genes such as HOXA7, HOXB3, HOXA3 are HOXB13 are involved in the control of endothelial differentiation control of human MSC.

Furthermore, analysis of HOX gene expression during in vitro differentiation of human MSC showed that HOXA7 and HOXB3 are significantly up-regulated whereas HOXA3 and HOB13 are significantly down-regulated in more differentiated progenitors (Chung et al., 2009).

Finally, extensive evidence suggests the key role of HOX proteins in bone tissue repair (Gersch et al., 2005).

While this data strongly suggests the role of HOX in controlling MSC functions, it is still observational data, limited by the lack of models that can implement knockout and knockdown studies and overexpression approaches to fully assess the functional role of HOX genes during tissue repair with the purpose of optimizing cell therapies (Mahdipour and Mace, 2011).

Since HOX genes act as transcription factors, they can specifically facilitate the production of further proteins, by binding to gene promoters through their DNA-interacting domain.

Previous studies on tumor cells show that HOXB7 can induce bFGF production (Carè et al., 2001).

Furthermore, when the growth factor bFGF is administered as a recombinant factor, it can facilitate cell proliferation and has an important function in differentiation (Tasso et al. 2012).

Nevertheless, extensive evidence shows that the recombinant protein has a limited stability in cell culture medium, and requires continuous supplementation or stability-increasing interventions. HOXB7 also activates production of further growth factors involved in various processes, inclusing VEGF, which is involved in angiogenesis (How et al., 2013).

Stem cells, possibly genetically modified for increasing production and secretion of biomolecules, have been used in experimental models with the purpose of promoting tissue regeneration, such as revascularization after myocardial infarction, regeneration of intervertebral disk defects, repair of infarcted tissues, repair of skeletal tissue and as an adjuvant in neurodegenerative diseases or for inhibiting tumor growth (Meyerrose et al., 2010).

Nevertheless, the regenerative potential of stem cells upon infusion into patients is temporary (Dominici et al., 2009; Li and Lin, 2012).

Ex-vivo expansion and human MSC performance optimization approaches have also been studied, by introducing the gene coding for telomerase enzyme protein (TERT), whose activity maintains the length of telomeres, chromosome end regions of highly repeated DNA, whose progressive shortening is likely associated with cell aging.

In addition to maintaining the length of telomeres, the ectopic expression of TERT in human MSC extends cell survival and delays senescence in vitro, and enhances bone formation in vivo, without leading to neoplasia formation (Simonsen et al., 2002).

Nevertheless, due to the immortalizing activity of TERT, further investigation is required to confirm safe use of such modified cells, which might potentially induce tumors and be thus unsuitable for human use.

DISCLOSURE OF THE INVENTION

One object of the invention is to improve the prior art.

Another object of the invention is to modify a cell by inducing it to overexpress the HOXB7 protein, to increase its proliferative capacity and reduce its senescence propensity, for optimized ex vivo expansion.

A further object of the invention is to extend the duration of therapeutic effectiveness of modified HOXB7-overexpressing cells upon in vivo infusion.

Another object of the invention is to facilitate tissue regeneration by utilizing the increased ability of HOXB7-overexpressing cells to produce bone tissue.

Yet another object of the invention is to obtain increased autocrine production of the growth factor bFGF by HOXB7-modified cells.

In one aspect, the invention provides a modified cell overexpressing the HOXB7 protein as defined in claim 1.

In a further aspect, the invention relates to a method of producing a modified HOXB7-overexpressing cell as defined in the features of claim 9.

The method of producing the modified cell provides:
a cell population that overexpresses the HOXB7 protein;
a higher proliferation of modified cells, for faster ex vivo expansion;
a cell population that can produce and secrete the growth factor bFGF in the culture medium;
a less senescent cell population;
a cell population with a higher differentiative potential, when appropriately stimulated for bone tissue production;
a cell population that can potentially facilitate bone regeneration in vivo.

In a further aspect, the invention provides the ability of acting upon human or animal cells by modulating the expression of endogenous HOXB7 protein, by overexpression or down-regulation of its specific miRNA regulators, miR-196a and miR-196b.

In a further aspect, the invention provides the ability of acting upon the genetic modification so introduced by adding the 3'-untranslated region (3'-UTR), downstream from the HOXB7-coding sequence for the protein to be susceptible to regulation by miR-196a.

Concerning the use of modified cells for growth factor expression, the invention can act at a higher regulation level, by controlling the expression of various proteins with the introduction of a single genetic sequence.

Concerning the use of modified cells for the TERT protein expression, the modification of the invention introduces a gene that can stimulate proliferation without immortalization.

Further aspects of the inventions are given in the dependent claims.

The invention achieves the following additional advantages:
faster expansion of the modified cells without immortalizing cells;
induction of multiple protein production by insertion of a single expression-controlling gene;
the possibility of controlling protein expression by specific microRNAs.

BRIEF DESCRIPTION OF FIGURES

Further features and advantages of the invention will be more readily apparent upon reading of the detailed description of preferred non-exclusive embodiments of a cell modified for HOXB7 overexpression, which is shown as a non-limiting example in the annexed drawings, in which:

FIG. 23 is a list of the differentially expressed microRNAs by less proliferating cells (P-) and more proliferating cells (P+);

FIG. 24 is a sequence (SEQ ID NO 2) that codes for the HOXB7 protein.

DETAILED DESCRIPTION OF A PREFERRED EMBODIMENT

According to the invention, a HOXB7-coding gene has been introduced, thereby generating a cell that can have greater proliferative potential, less senescence and increases differentiative potential relative to controls having no HOXB7-overexpression modification.

Gene Modification of Cells with HOXB7 Gene

This approach consists in gene modification of cells using gene sequences, known as "vectors" that can induce the expression of proteins, known as HOX.

Figure 1:
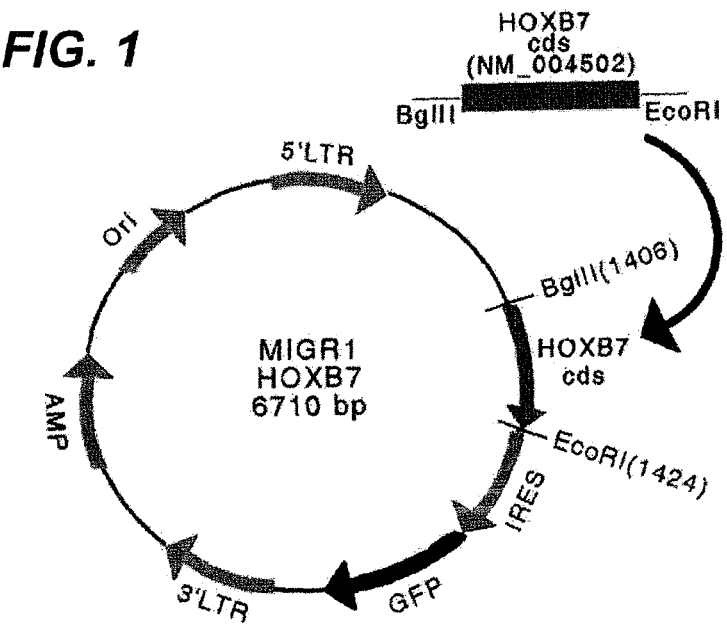
FIG. 1 is a schematic representation of the construct that was used for the genetic modification of cells.

As shown in FIG. 1, the HOXB7 protein-coding sequence is introduced into the circular plasmid DNA sequence MIGR1 using the insertion sites BgIII and EcoRI.

The plasmid DNA contains the GFP protein-coding sequence which will be used as a label to check that the modification has been made.

HOX genes are transcription factors (i.e. factors that can bind DNA and promote synthesis of other proteins) that can influence proliferation and differentiation of human cells during pre- and postnatal life.

The insertion of HOXB7 protein-producing vectors affords the production of modified cells having increased growth, while facilitating their differentiation toward bone.

Creation of the Construct

The HOXB7 coding gene was produced and amplified by polymerase chain reaction (PCR) from total RNA extracted from hematopoietic cells and corresponds to the sequence filed in PubMed database with the code NM_004502.

The sequence so obtained was inserted into a retroviral vector by enzyme digestion and cloning, as shown in FIG. 1.

A population of carrier cells that can stably produce a pool of retroviral particles capable of infecting the cell population of interest was created through two steps.

The first step is based on the obtainment of a cell line producing the retrovirus in transient mode and the second step is aimed at obtaining the generation of a Producer Cell Line (PCL) capable of stably producing a retroviral progeny.

For the transient step, embryonic renal fibroblasts (293T cells) were transfected with plasmid DNA with the help of polycations to produce a supernatant containing the retroviral particles.

The retroviral supernatant was collected and used to infect the PLC deriving from a human fibrosarcoma line: 24 hours after infection the cells were analyzed by cytofluorimetry to check positivity of green fluorescent protein (GFP), an infection efficiency marker.

The viral supernatant that was in turns stably produced by the PLCs was used to infect the cells of interest.

Transformation of HOXB7-Overexpressing Cells

The cells of interest were isolated from bone marrow aspirations by density gradient centrifugation (Ficoll) and were selected according to their ability of adhering to the plastic medium upon which they are cultivated in vitro.

The cells underwent three infection cycles using the retroviral supernatants produces by the PLCs.

Then infection efficiency was assessed by analysis of the expression of the green fluorescent protein (GFP).

Figure 2:
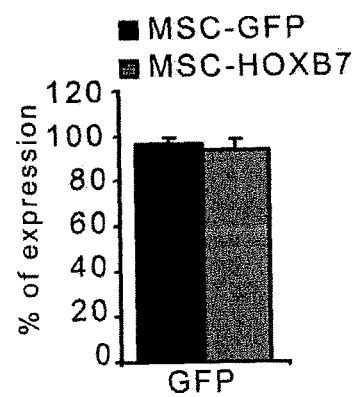
FIG. 2 is a chart showing an efficiency analysis of cell transduction using the construct by assessment of the amount of fluorescence emitted by the green fluorescent protein (GFP) coded by the vector in use.

As shown in FIG. 2, this analysis indicates that all the cells were successfully modified (gray bar), similarly to the GFP control (black bar).

Assessment of Overexpression

Figure 3:
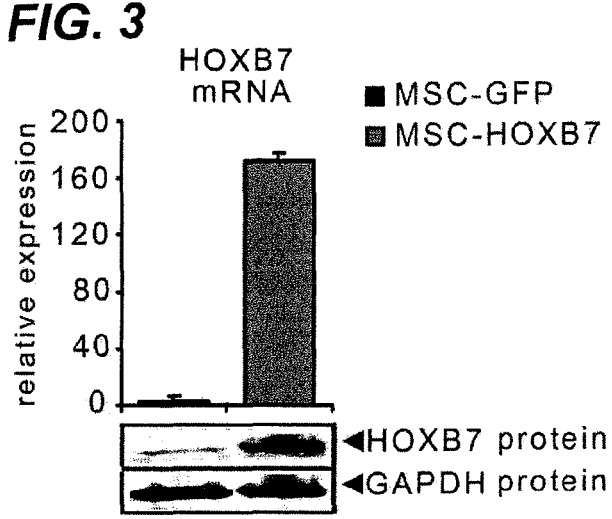
FIG. 3 is a chart showing the analysis of HOXB7 expression in modified cells, assessed both as messenger (mRNA) production by real time PCT and as a protein by Western Blotting.

HOXB7 protein overexpression was verified by quantitative PCR and Western Blotting (FIG. 3).

Quantitative PCR allowed detection of relative expression levels of the mRNA of HOXB7 (>160 fold the control infected with the empty vector, i.e. a vector not containing the HOXB7 coding sequence, while Western Blotting allowed detection of the higher expression of HOXB7, normalized to an endogenous protein constitutively expressed by the cells of interest (GAPDH).

Impact of Overexpression on Morphology and Antigen Expression

Figure 4:
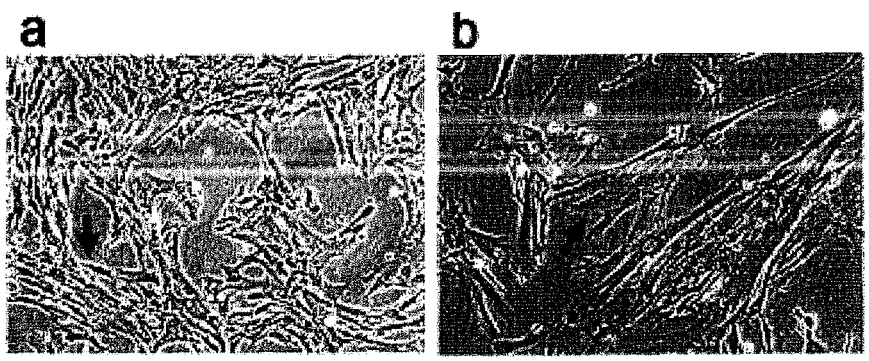
FIG. 4 shows microscopy images showing primary cells modified for higher HOXB7 expression (image a) and corresponding GFP controls (image b), in which the arrows that indicate the individual cells highlight a smaller cell size in image (a) than in image (b)
Figure 5:
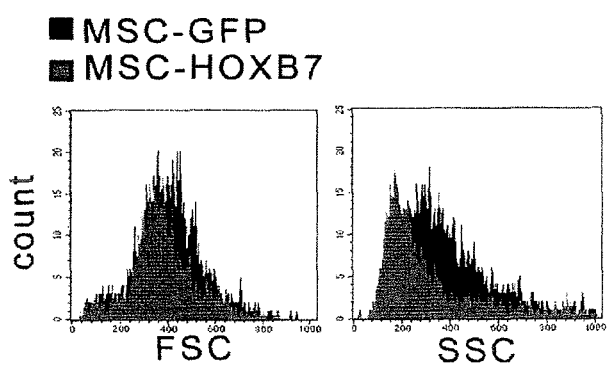
FIG. 5 is a chart showing the cytofluorimetric analysis of the physical parameters FSC and SSC, indicating cell size and internal complexity respectively.

The morphology of the modified cells was assessed by inverted microscope observation and by cytofluorimetry (see FIG. 4 and FIG. 5).

HOXB7-overexpressing cells are morphologically different from the control, and particularly have a smaller size and a lower degree of internal complexity, as shown in FIG. 4 by arrows and in FIG. 5, which shows the values of FSC and SSC.

The FSC value reflects cell size and SSC values reflect internal complexity, and both are lower for HOXB7-modified cells (gray bar) than for GFP control cells (black bar).

Therefore, the cells modified for HOXB7 overexpression are smaller and less complex cells.

The cells modified for HOXB7 overexpression have a particular in vitro growth, with a cord arrangement (see FIG. 4(a)).

Figure 6:
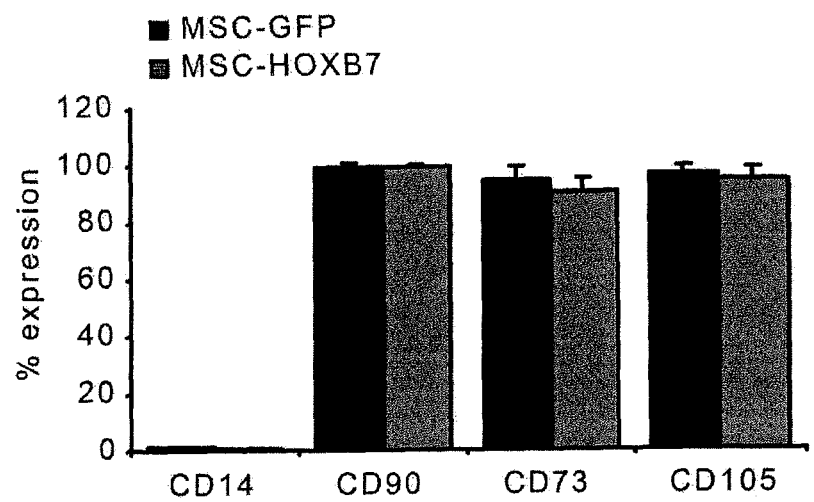
FIG. 6 is a chart showing the cyrofluorimetric analysis of characterizing surface antigens that characterize the cells being used and in which the modification has been made.

The surface markers typically expressed by the cell, CD90, CD73 and CD105 are maintained as shown in FIG. 6, with the chart showing that these markers undergo no relevant change due to the modification.

Assessment of Proliferation, Clonogenicity and Senescence

HOXB7-modified cells acquire a higher proliferative potential, which is assessed as an expression of the cell proliferation marker Ki67.

Ki67 is a cell proliferation marker, and its quantity reflects cell growth.

Figure 7:
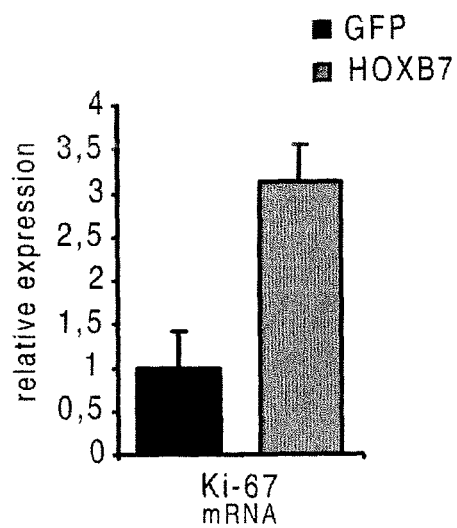
FIG. 7 is a chart that shows the analysis of Ki67 mRNA expression by real time PCR.

As shown in FIG. 7, the cells modified for HOXB7 overexpression have higher levels of Ki67.

The greater proliferation was also assessed by microscopic cell counting during in vitro expansion.

Figure 8:
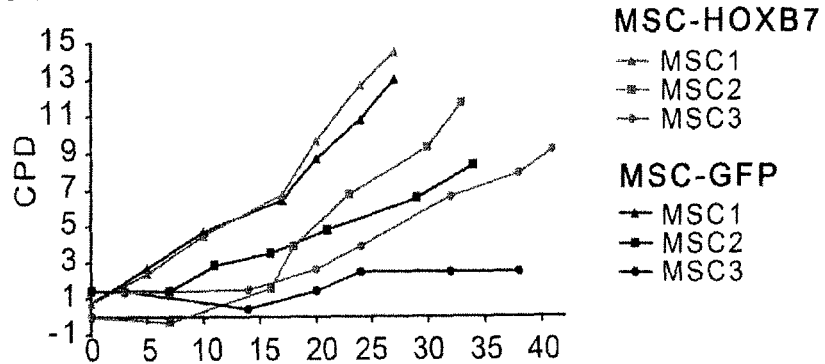
FIG. 8 is a chart for in vitro cell proliferation and growth assessment of modified cells by microscopic cell counting.

FIG. 8 shows the higher proliferative capacity of HOXB7-modified cells as compared with GFP controls.

Figure 9:
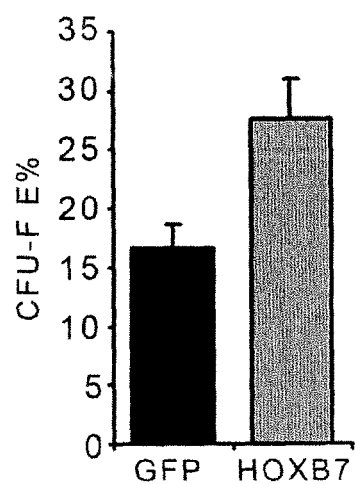
FIG. 9 is a chart for the assessment of clonogenic efficiency, i.e. in vitro colony-forming ability of cells.

Furthermore, the cells modified for HOXB7 overexpression have a greater colony formation efficiency (CFU-F) as compared with GFP control (see FIG. 9).

Senescence monitoring by beta glactosidase staining allowed detection of a significantly smaller number of senescent cells in HOXB7-modified cultures.

Figure 10:
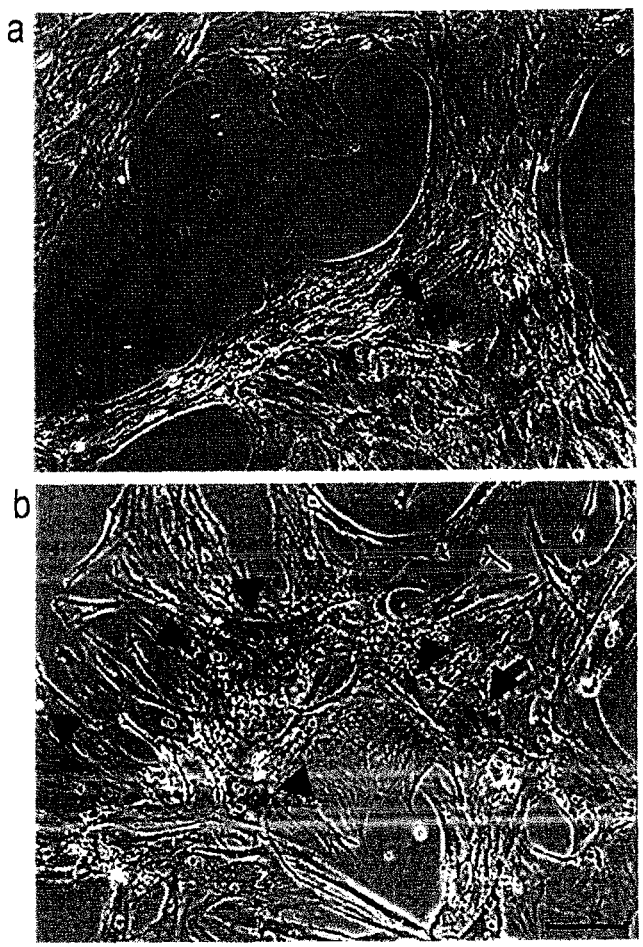
FIG. 10 shows microscopy images of beta galactosidase-stained cells, identifying senescent cells, in which HOXB7-modified cells exhibit less senescence than GFP control cells.

FIG. 10 shows the smaller number of senescent cells (beta-galactosidase positive cells, i.e. stained and indicated by arrows) among modified cells (a) relative to control cells (b).

Figure 11:
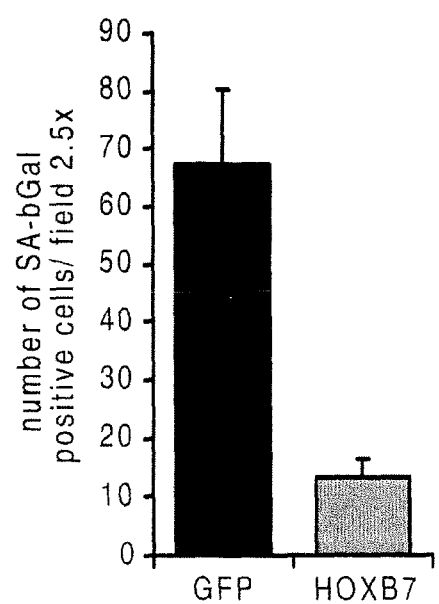
FIG. 11 is a chart for quantification of beta galactosidase positive cells, i.e. senescent cells, in the cultures of the modified cells.

Referring to FIG. 11, the quantification of stained, senescent cells shows that the GFP control cell population contains a greater number of senescent cells than the cell population modified for HOXB7 overexpression.

Detection of FGF Levels in HOXB7-Overexpressing Cells

Figure 12:
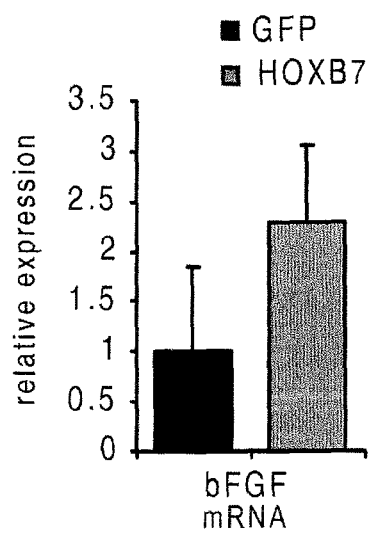
FIG. 12 is a chart showing the expression of the growth factor bFGF mRNA produced by the modified cells.
Figure 13:
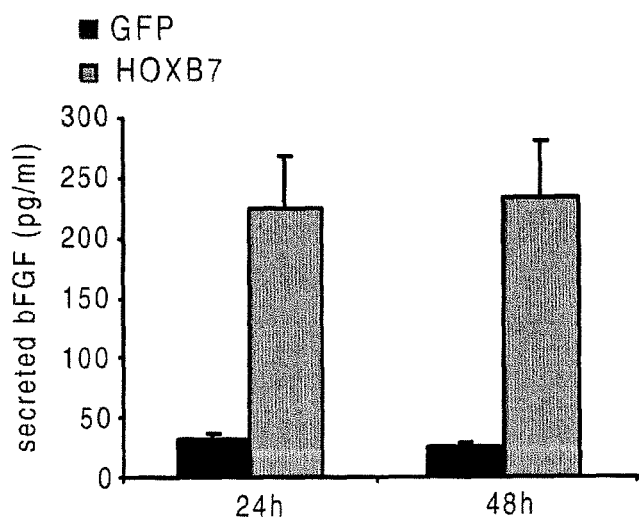
FIG. 13 is a chart for ELISA assessment of the amount of bFGF protein released by the modified cells.

HOXB7-overexpressing cells produce higher measured bFGF levels, a growth factor also known as FGF2, both as mRNA expression by real time PCR, as shown in FIG. 12, and as a secreted protein as measured by ELISA, whose values are shown in the chart of FIG. 13.

In greater detail, secretion of the bFGF protein was found to be 4.3 to 8.2 fold higher in HOXB7-modified cells than in the GFP control.

Assessment of Osteogenic Differentiation

The modified cells were induced to form bone tissue using a conditioned medium containing dexamethasone, ascorbic acid, beta-glycerophosphate and BMP2 (the latter being added at day seven), and were found to have a higher bone-forming ability relative to the control.

Particularly, the modified cells produce a significantly greater amount of mineralized matrix, as assessed by Von Kossa staining in vitro.

Von Kossa is a dye that is known to identify calcium deposits released from osteogenically differentiating cells.

Figure 14:
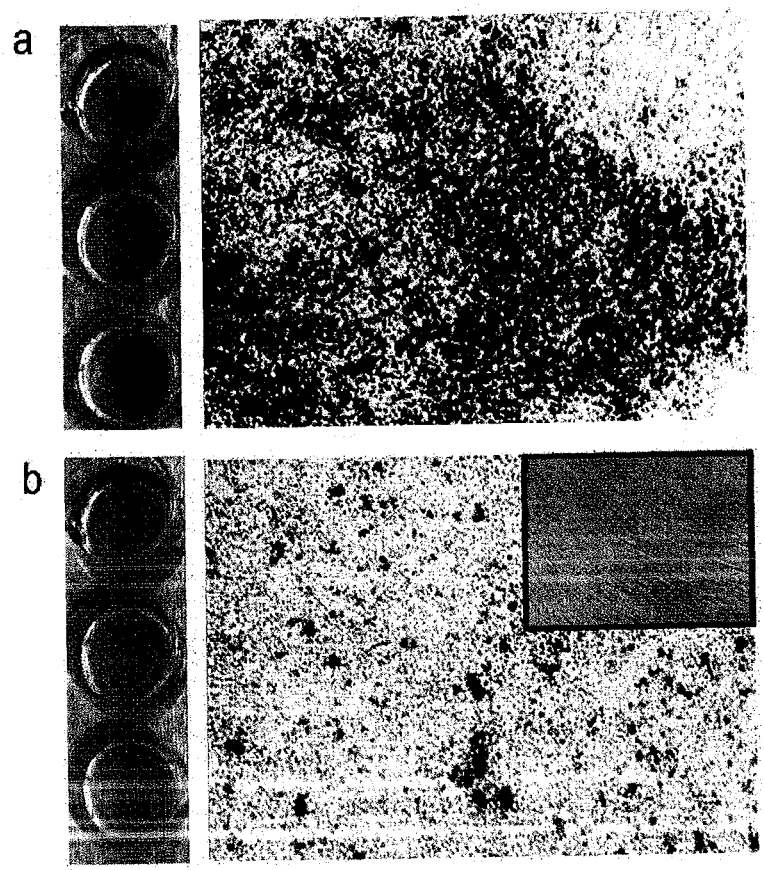
FIG. 14 is a microscopy image of Von Kossa staining.

As shown in FIG. 14, the cells modified for HOXB7 overexpression (a) are more stained than the GFP control (b).

Figure 15:
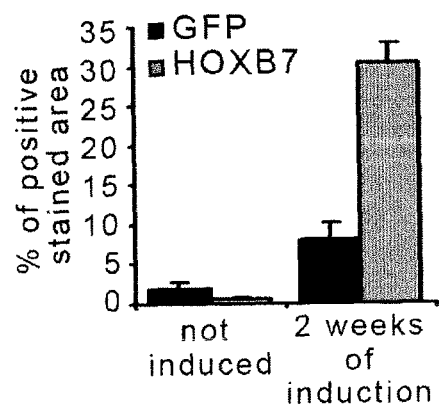
FIG. 15 are charts showing the quantification of stained deposits in the modified cells.

Furthermore, particularly referring to FIG. 15, Von Kossa staining quantification shows that HOXB7-overexpressing cells (gray bar) produce 8.5 to 12.2 fold increased levels of calcium deposits as compared with GFP control cells (black bar) after 2 weeks' induction, or maintenance of cells in an appropriate bone production-stimulating culture medium.

Figure 16:
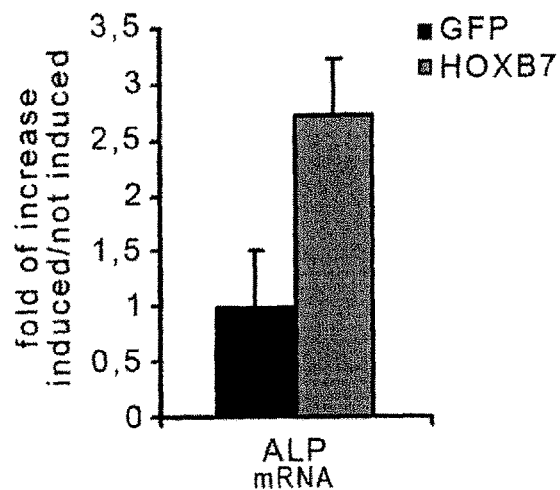
FIGS. 16, 17 and 18 are charts that shows the expression of alkaline phosphatase bone tissue markers (ALP), collagene 1 (Col1A1) and decorin (DCN), in which the black color indicates the controls, i.e. the cells modified with an empty vector, which express GFP but not HOXB7 and the gray color indicates the cells modified for higher HOXB7 expression.
Figure 17:
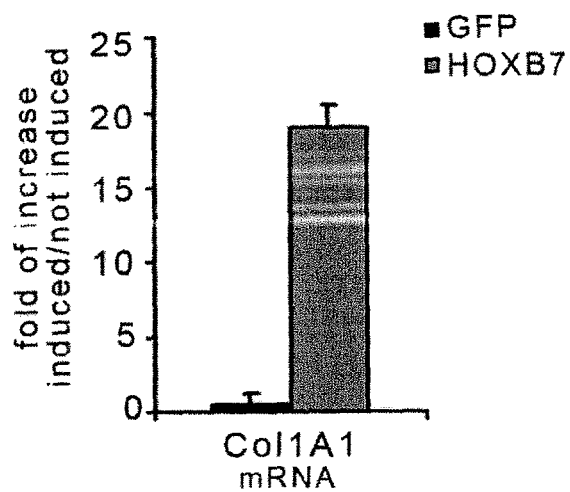
Figure 18:
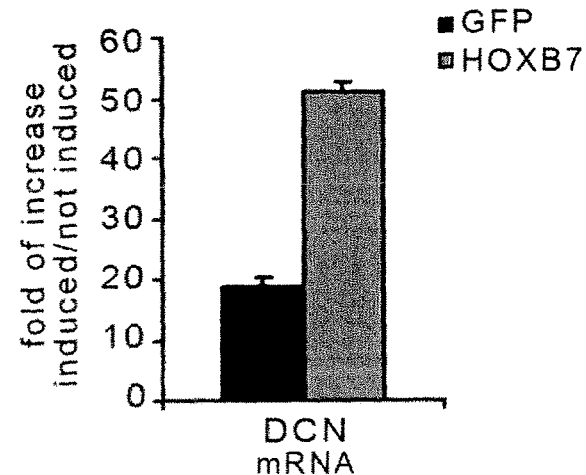

The modified cells show a higher expression of alkaline phosphatase molecular markers (ALP), alpha-1 type I collagen (Col1A1) and decorin (DCN), as shown in FIG. 16, FIG. 17 and FIG. 18.

In greater detail, the change in the expression of these markers is found to be 2.7 to 41 fold higher in HOXB7-modified cells than in GFP controls.

Identification of Expression Control Mechanisms

MicroRNAs are small RNAs that regulate gene expression by specific recognition of 3' untranslated regions (3' UTR) of messengers (mRNA).

Figure 19:
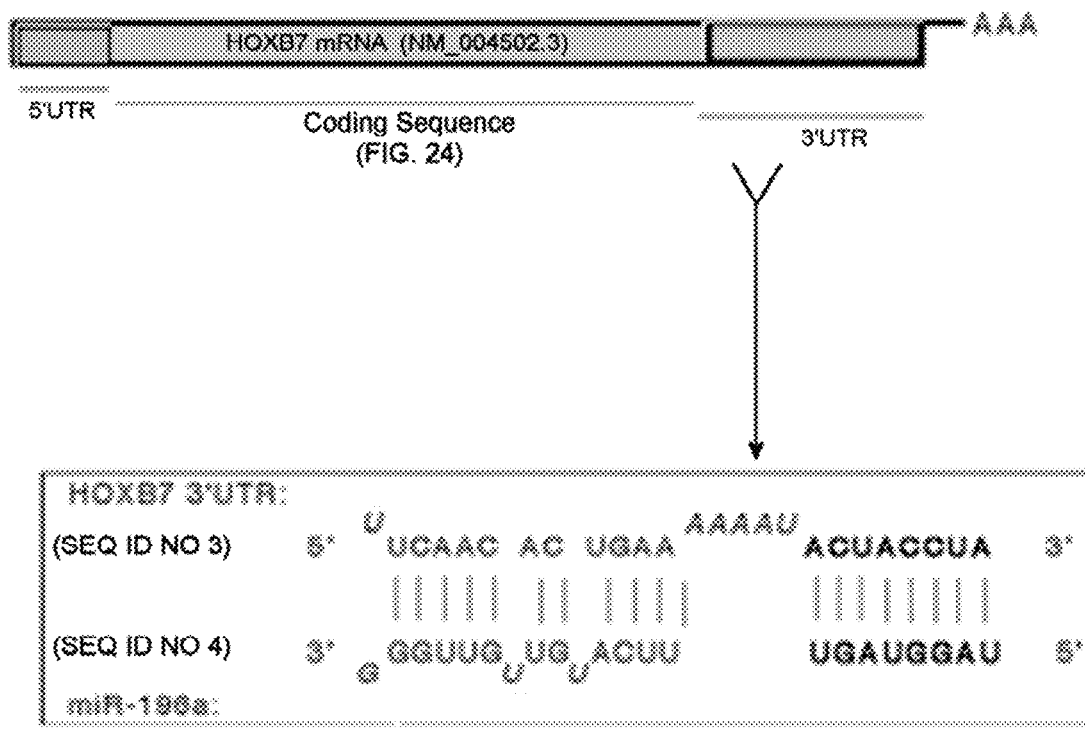
FIG. 19 is a diagrammatic representation of the 3' UTR (3' untranslated region) sequence of the HOXB7 gene (SEQ ID NO 1), allowing microRNA-mediated protein expression control; the 3' UTR sequence of HOXB7 is paired to the microRNA 196 (miR-196) sequence, which prevents HOXB7 protein production (see panel).

Using predictive algorithms we identified miR-196a as a potential molecule that can regulate HOXB7 expression (FIG. 19).

Figure 20:
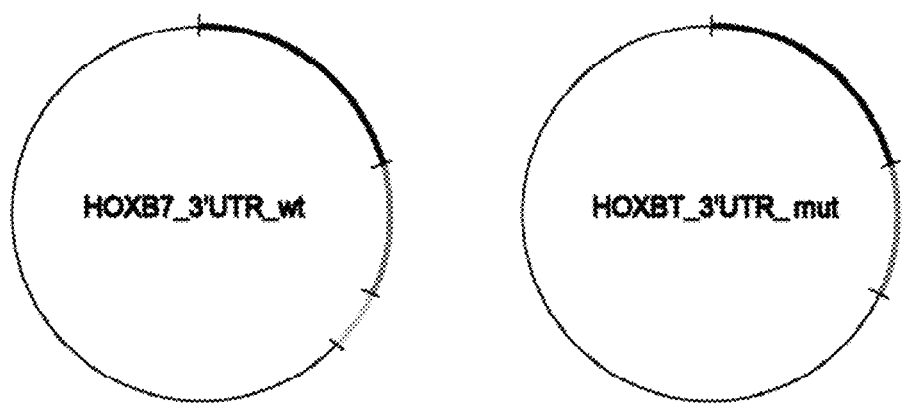
FIG. 20 is the diagrammatic representation of the constructs that have been used to show that the expression of HOXB7 gene is regulated in sequence-specific manner by the microRNA miR-196a; the construct expresses luciferase, an enzyme whose action causes a light emission and upstream from the enzyme-coding sequence the HOXB7 3' UTR region or the deleted 3' UTR sequence for the above region of interaction with miR-196 (HOXB7 3' UTR 99-227) has been placed to show the direct interaction therebetween.
Figure 21:
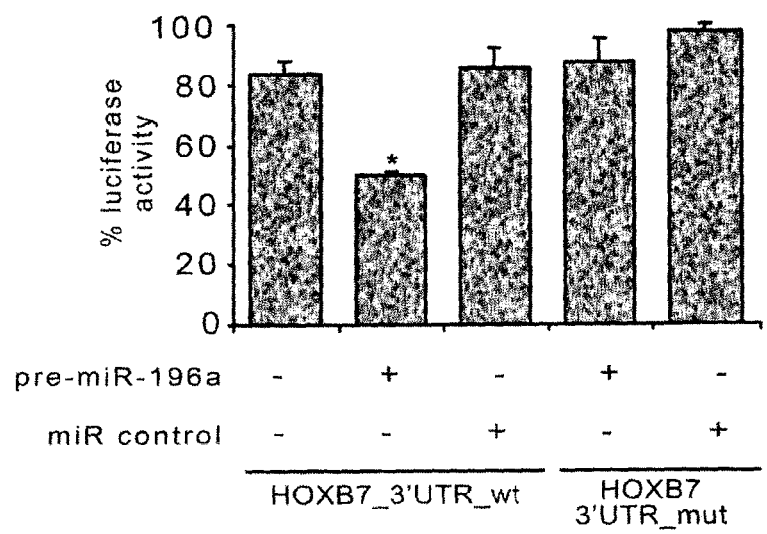
FIG. 21 is a chart showing luciferase expression assessment by measurement of the light emission of luciferin upon introduction of miR-196a or control (miR control) into the cells transduced for the constructs as shown in FIG. 20.

A luciferase assay was used to show that miR-196 directly targets the 3' UTR region of HOXB7 in cells, and hence can specifically control its expression (FIG. 20 and FIG. 21).

Referring to FIG. 21, the presence of miR-196 is found to reduce light emission (column two) due to the specific interaction of miR-196 with the 3' UTR sequence of HOXB7.

Identification of Differentially Expressed MicroRNAs of Less Proliferating Cells and More Proliferating Cells, as a Prediction of Cell Performance A set of microRNAs was identified, with microRNAs differentially expressed by cells with different proliferative potentials (P− and P+).

Figure 22:
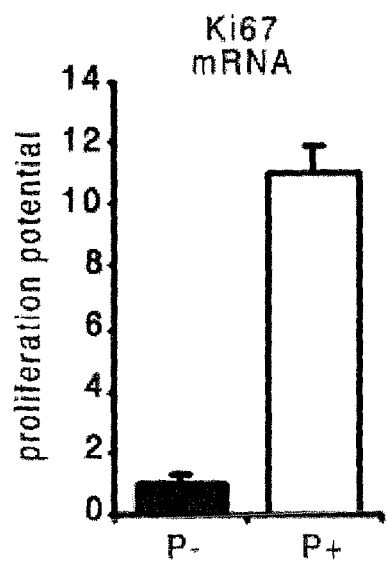
FIG. 22 is a chart showing a higher Ki67 expression in the P+ group than in the P- group.

Referring to FIG. 22 the P− group expresses lower levels of Ki67, thereby exhibiting a lower proliferative potential, and the P+ group expresses higher levels of Ki67, thereby exhibiting a higher proliferative potential.

These two groups with different proliferative potentials show differences in mRNA expression: miR-99, miR-100, miR-196, miR-337-5p, miR-376, miR-431, miR-543 as shown in FIG. 23. This microRNA set may be used to obtain information about cell proliferation capacity.

The invention has been found to fulfill the intended objects.

The invention so conceived is susceptible to changes and variants within the inventive concept.

Furthermore, all the details may be replaced by other technically equivalent elements, without departure from the scope as defined by the following claims.

The invention claimed is:

1. A method of obtaining over-expression of a HOXB7 protein encoded by a nucleotide sequence having SEQ ID NO 2 within mesenchymal stem cells (MSCs) to form skeletal tissue, comprising:
   yielding retroviral particles carrying a coding sequence for said HOXB7 protein; and
   genetically modifying said MSCs by infecting said MSCs with said retroviral particles to produce modified cells having a faster expansion, a lower senescence rate, and an increased ability to form said skeletal tissue than the MSCs before infecting
   wherein said MSCs comprise isolated MSCs of human origin chosen from bone marrow, fat, umbilical cord, menstrual liquids, amniotic liquid, synovial liquid, tooth pulp, hepatic tissue, pulmonary tissue, or pancreatic tissue.

2. The method as claimed in claim 1, further comprising a step of inducing said genetically modified MSCs to express higher levels than the MSCs before infecting of one or more of alkaline phosphatase molecular markers (ALP), alpha-1 type I collagen (Col1A1), or decorin (DCN).

3. The method as claimed in claim 2, wherein inducing said genetically MSCs to express higher levels than the MSCs before infecting comprises inducing said genetically modified MSCs with a conditioned medium containing dexamethasone, ascorbic acid, beta-glycerophosphate, and bone morphogenetic protein 2 (BMP2).

4. The method as claimed in claim 2, wherein the step of inducing said genetically modified MSCs to express higher levels than the MSCs before infecting of one or more of alkaline phosphatase molecular markers (ALP), alpha-1 type I collagen (Col1A1), or decorin (DCN) comprises a step of inducing said genetically modified MSCs to form the skeletal tissue with the lower senescence rate.

5. The method as claimed in claim 1, wherein said genetically modified MSCs have an increased production or an increased release of growth factors than unmodified MSCs, and wherein at least one of said growth factors is bFGF.

6. The method as claimed in claim 1, further comprising:
   collecting a retroviral supernatant from embryonic renal fibroblast cells;
   infecting a Producer Cell Line of a human fibrosarcoma line; and
   analyzing after 24 hours by cytofluorimetry a positivity percentage of green fluorescent protein,
   wherein infecting said MSCs with said retroviral particles comprises infecting said MSCs with retroviral supernatant produced by said Producer Cell Line.

* * * * *

```
                              SEQUENCE LISTING

<160> NUMBER OF SEQ ID NOS: 4

<210> SEQ ID NO 1
<211> LENGTH: 473
<212> TYPE: DNA
<213> ORGANISM: Homo sapiens

<400> SEQUENCE: 1
aggaggagga agaggaagag tgagggatgg agaaagggca gaggaagaga catgagaaag     60
ggagaggaag agaagcccag ctctgggaac tgaatcagga aactcaaatc gaatagggaa    120
gtaaaaaaac aaaacaaaaa acaaaaaaaa caaaaaaaaa accctattta aatgaaagga    180
gtttaaaaac atttttttaag gagggagaaa ggagaaattt tggtttttca acactgaaaa    240
aatactacct ataggaaagt ctgtcaggtt tggttttttt gtacaatatg aaaaggatat    300
tatctacctg ttctgtagct ttctggaatt tacctccccct tttctatgtt gctattgtaa    360
ggtctttgta aaatcttgca gttttgtaag ccctctttaa tgctgtcttt gtggactgtg    420
ggtctggact aaccctgtgg ttgcctgccc tcctgagcct ccgccttccc agc           473

<210> SEQ ID NO 2
<211> LENGTH: 654
<212> TYPE: DNA
<213> ORGANISM: Homo sapiens

<400> SEQUENCE: 2
atgagttcat tgtattatgc gaatactttta ttttctaaat atccagcctc aagttcggtt     60
ttcgctaccg gagccttccc agaacaaact tcttgtgcgt ttgcttccaa cccccagcgc    120
ccgggctatg gagcgggttc gggcgcttcc ttcgccgcct cgatgcaggg cttgtacccc    180 ggcgggggg gcatggcggg ccagagcgcg gccggcgtct acgcggccgg ctatgggctc    240
gagccgagtt ccttcaacat gcactgcgcg ccctttgagc agaaccctctc cggggtgtgt    300 cccggcgact ccgccaaggc ggcgggcgcc aaggagcaga gggactcgga cttggcggcc    360
gagagtaact tccggatcta ccctggatg cgaagctcag gaactgaccg caaacgaggc    420
cgccagacct acacccgcta ccagaccctg gagctggaga agaatttca ctacaatcgc    480 tacctgacgc ggcggcggcg catcgagatc gcgcacacgc tctgcctcac ggaaagacag    540
atcaagattt ggtttcagaa ccggcgcatg aagtggaaaa aggagaacaa gaccgcgggc    600
ccggggacca ccggccaaga cagggctgaa gcagaggagg aagaggaaga gtga           654

<210> SEQ ID NO 3
<211> LENGTH: 25
<212> TYPE: RNA
<213> ORGANISM: Homo sapiens

<400> SEQUENCE: 3
uucaacacug aaaaaauacu accua                                           25

<210> SEQ ID NO 4
<211> LENGTH: 22
<212> TYPE: RNA
<213> ORGANISM: Homo sapiens
```

```
<400> SEQUENCE: 4
uagguaguuu cauguuguug gg                                                22
```